United States Patent [19]

Mead et al.

[11] Patent Number: 5,163,519
[45] Date of Patent: Nov. 17, 1992

[54] PNEUMATICALLY DRIVEN REVERSE IMPACT DEVICE

[75] Inventors: Donald R. Mead, Jupiter; Alvin L. Knoll, Loxahatchee, both of Fla.

[73] Assignee: Florida Pneumatic Manufacturing Corp., Jupiter, Fla.

[21] Appl. No.: 833,062

[22] Filed: Feb. 10, 1992

[51] Int. Cl.$^5$ .................. B25D 9/02; B25D 17/06
[52] U.S. Cl. ...................... 173/91; 173/135; 173/211; 29/254
[58] Field of Search ............ 173/91, 92, 114, 135, 173/211; 29/254, 255, 261, 262

[56] References Cited

U.S. PATENT DOCUMENTS

| | | | |
|---|---|---|---|
| 618,324 | 1/1899 | Blum | 173/91 |
| 1,292,429 | 1/1919 | Bull | 173/91 |
| 2,561,577 | 7/1951 | Knudsen | 29/254 |
| 3,739,452 | 6/1973 | Gadberry | 29/254 |
| 4,114,950 | 9/1978 | Cooper | 173/91 |
| 4,586,230 | 5/1986 | Harydzak et al. | 29/254 |

Primary Examiner—Douglas D. Watts
Assistant Examiner—Scott A. Smith
Attorney, Agent, or Firm—George C. Atwell

[57] ABSTRACT

A device for removing pins, nails, dowels, rods, and the like from material which includes wood, metal, concrete, and human and animal bone, includes a pneumatically actuated piston producing a reverse impact striking effect which causes extraction of the pin from the material. The device includes a main housing comprising a tool handle, an elongated barrel partially mounted in the tool handle, and a muffler housing fitted on the barrel and abutting the tool handle. A central chamber extends the length of the barrel, and disposed within the central chamber is a shaft which is adapted for linear reciprocal movement therein. An anvil is mounted at the inner end of the shaft and a tool holder is mounted at the opposite end of the shaft. Slidably disposed on the shaft is a piston which is adapted for linear reciprocable movement thereon for forcibly striking the anvil. An upper valve block, a lower valve block, and a flipper valve positioned therebetween are located within the tool handle adjacent the anvil for directing pressurized air from an external source into the central chamber, and concomitant with the exhaustion of air from the central chamber, causes the slidable movement and the reverse striking impact of the piston against the anvil, thus effecting pin removal.

10 Claims, 5 Drawing Sheets

PNEUMATICALLY DRIVEN REVERSE IMPACT DEVICE

BACKGROUND OF THE INVENTION

The device of the present invention pertains to the removal of nails, pins, or dowels from a material, and more particularly pertains to the use of a pneumatic, reverse striking device for pulling nails, pins, or threaded dowels embedding in plastic, concrete, metal, or bones as a result of orthopedic surgery.

The use of fluid actuated or pneumatic actuated devices to extract a workpiece embedded in a material is well known in the prior art. Two examples are the Hartenbach patent, Swiss patent 301,236, and the Schmidt patent, U.S. Pat. No. 3,511,325.

The Hartenbach patent discloses a device which exerts a uniform pulling motion on a pin which is to be removed from a bone. In order to exert the uniform pulling motion on the pin, the device utilized mechanical, hydraulic, pneumatic or electric means to produce rapid striking pulses which cause removal of the pin from the bone. Compressed air is used to drive a cylinder upward to strike a piston, this striking effect as a consequence being transmitted to a pull rod and an intermediate member attached to the bone.

The Schmidt patent discloses a device for extracting sheet piles and jammed drill rods from material. The device includes a tension rod for attachment to the structure to be extracted and a crosshead which is mounted to the top of the tension rod. The device includes a cylinder and within the cylinder is a reciprocable piston. The lower surface of the crosshead has an annular recess which defines a buffer chamber. A buffer liquid, such as hydraulic oil, fills the buffer chamber and absorbs the impact of the piston at the end of the piston's working stroke.

Despite the ingenuity of the above devices, there remains a need for a more efficient and effective device for pulling or extracting nails, pins, and the like from material such as human or animal bone, wood, concrete, or metal.

SUMMARY OF THE INVENTION

The device of the present invention is utilized for removing a workpiece, such as variously-sized nails, pins, rods, dowels, etc., from material which can include metal, concrete, wood, and human and animal bone. The device of the present invention is pneumatically driven for pulling or extracting pins and the like from material by a reverse-impact striking effect.

In the preferred embodiment, the device includes a main housing comprising an elongated, generally cylindrical tool handle having an air distribution chamber in air flow communication with an air passage inlet located at a handle gripping end of the tool handle. An air supply hose from an external air compressor is attached to the air passage inlet so that pressurized air can be delivered to the air distribution chamber of the tool handle.

An elongated, generally cylindrical barrel is adapted for securement into the tool handle with a substantial portion of the barrel projecting out of the tool handle and terminating at a tool holding end. The barrel has an elongated inner bore defining a central chamber extending therethrough and a lateral side passage extending substantially the same length as the central chamber. Both the side passage and the central chamber are in air flow communication with the air distribution chamber of the tool handle. In addition, the barrel has a plurality of exhaust ports to permit air to be exhausted to the atmosphere.

A generally cylindrical muffler housing fits onto the barrel and abuts the tool handle. The muffler housing has a plurality of muffler ports which permit air to be exhausted to the atmosphere.

At the tool holding end of the main housing is secured a generally cylindrical tool holder. More specifically, the tool holder is inserted into the inner bore of the barrel and partially protrudes out of the barrel. The tool holder has a partially threaded conical-shaped, tapered tool holder bore which can receive variously-sized cap screw adapters. If the pin or dowel has a tapped hole, a cap screw can be threaded into the tapped hole and the milled pocket of the cap screw adapter can receive the head of the cap screw.

The device of the present invention also includes a valve regulation means for regulating and directing the flow of pressurized air into the central chamber. The valve regulation means is located within the air distribution chamber and comprises an upper valve block, a lower valve block, and a flipper valve disposed therebetween to float as a consequence of the pressure variations occurring in the central chamber of the barrel and the continuous ingress of air into the air distribution chamber.

In addition, the upper and lower valve blocks each have a central aperture and lateral air passages which direct pressurized air into the central chamber and side passage coincident with air pressure variations occurring in the central chamber. The flipper valve is sandwiched between the upper and the lower valve blocks and is adapted to float axially therebetween directing air flow to either end of the central chamber concomitant with pressure variations occurring in the central chamber.

The device of the present invention also includes an elongated shaft disposed within the central chamber and having substantially the same length as the central chamber. The shaft extends to the tool holding end and provision is made for clearance between the inner end of the shaft and the lower valve block. The tool holder is mounted to the outer end of the shaft, and a cylindrical anvil is mounted to the inner end of the shaft adjacent the valve regulation means. The anvil has a plurality of spaced-apart through holes for allowing pressurized air flow therethrough and a tapered anvil bore within which the shaft is mounted.

A piston is slidably disposed on the shaft and is adapted for linear reciprocal movement thereon within the central chamber. When the device is disposed in its operative position, the piston forcibly slides on the shaft by pressurized air entering either end of the central chamber. The piston forcibly strikes the anvil at the end of the power stroke, and this reverse impact causes the shaft, the tool holder, and the pin, nail, or dowel attached to the tool holder to be pulled away from the material in which the pin has been embedded. The reverse impact of the piston striking against the anvil thus causes extraction or removal of the embedded pin, nail, or dowel.

The present invention also includes two pairs of tapered half-circle-shaped mounting clips, with a pair of clips mounted to the inner end and the outer end, respectively, of the shaft. When each pair of clips is disposed on the shaft, they form a cylindrical, tapered outer surface which matches and is wedged against the tool holder bore and the anvil bore. Thus, the need to pin, weld, or thread the tool holder and the anvil to the shaft is obviated by pressing the tool holder and the anvil onto the clips. The clips are wedged firmly against the shaft, and the tool holder and anvil are held securely on the shaft by being pressed firmly onto each respective pair of clips.

It is an objective of the device to permit the user to quickly and efficiently remove embedded pins, nails, and the like from material, such as wood, metal, concrete, and animal and human bone.

It is another objective of the device to provide a means whereby the tool holder can be attached to variously-sized cap screws which have been threaded into the tapped holes of dowels, pins, and the like.

Yet another objective is to utilize the retaining clips on each end of the shaft to firmly and securely mount the anvil and the tool holder to the shaft, thus relieving the stress on the shaft during pin removal and alleviating side loading on the shaft.

The device according to the invention will be described more in detail in the following specification with reference to the accompanying drawings.

DETAILED DESCRIPTION OF THE PREFERRED EMBODIMENT

Figure 1:
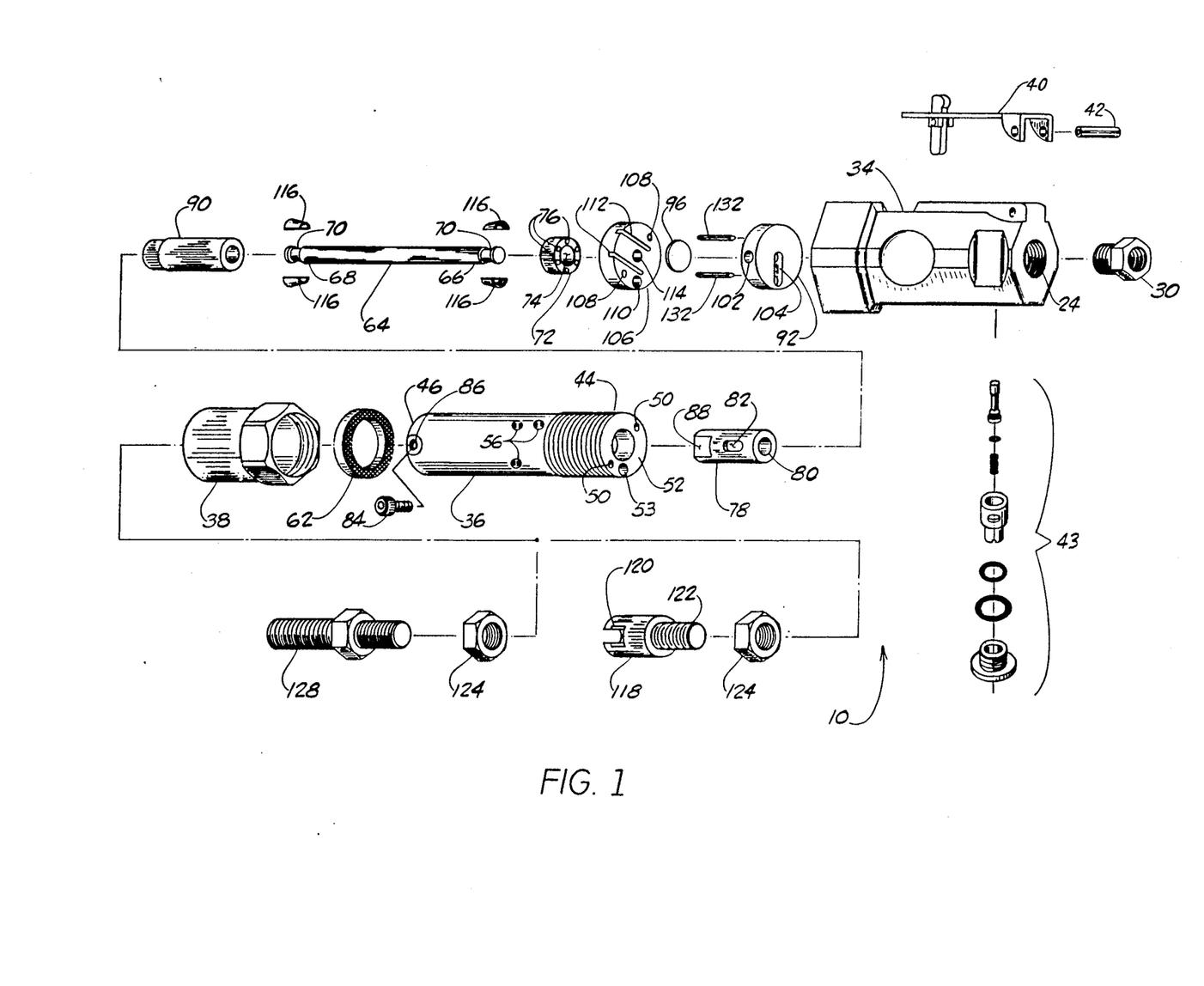
FIG. 1 is an exploded isometric drawing of the reverse impact pneumatic hammer device of the present invention.
Figure 2:
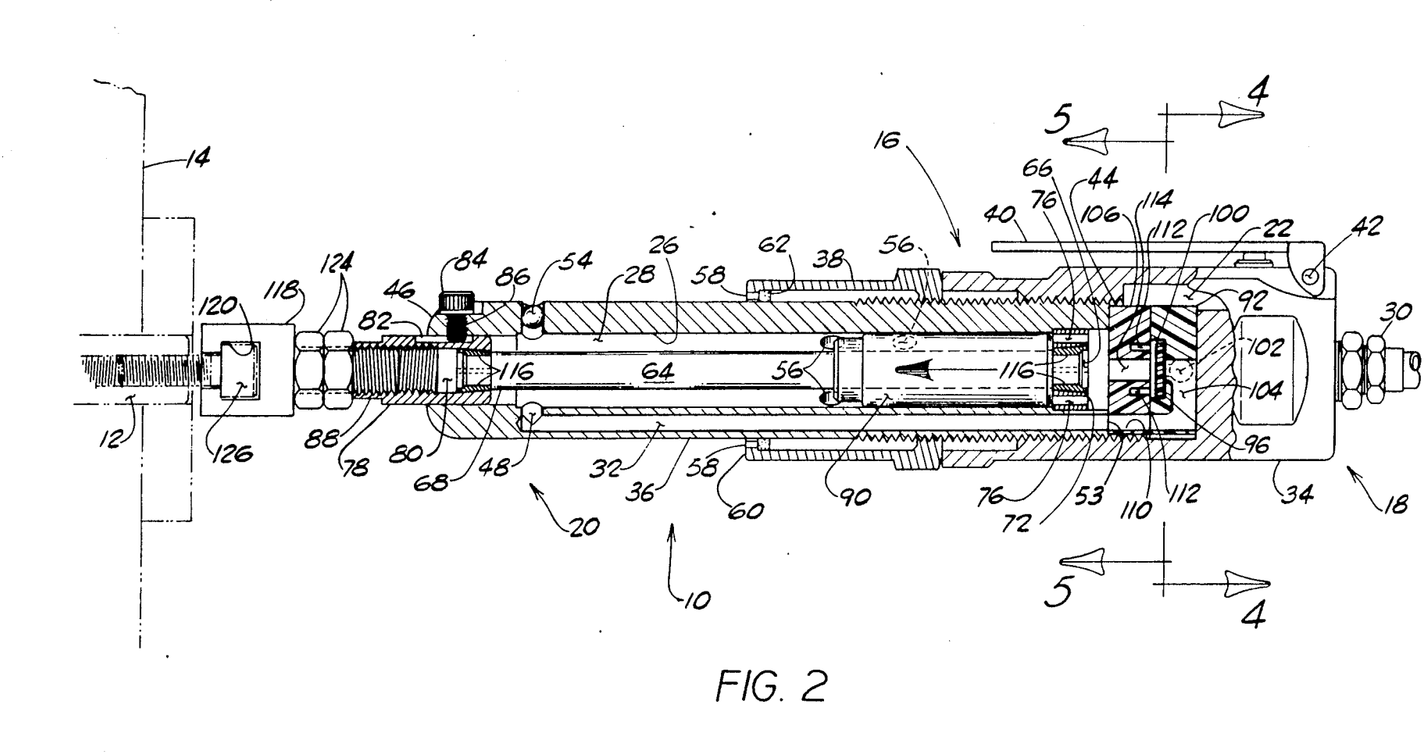
FIG. 2 is a longitudinal cross-sectioned view of the device first shown in FIG. 1, illustrating the power stroke of the device.
Figure 3:
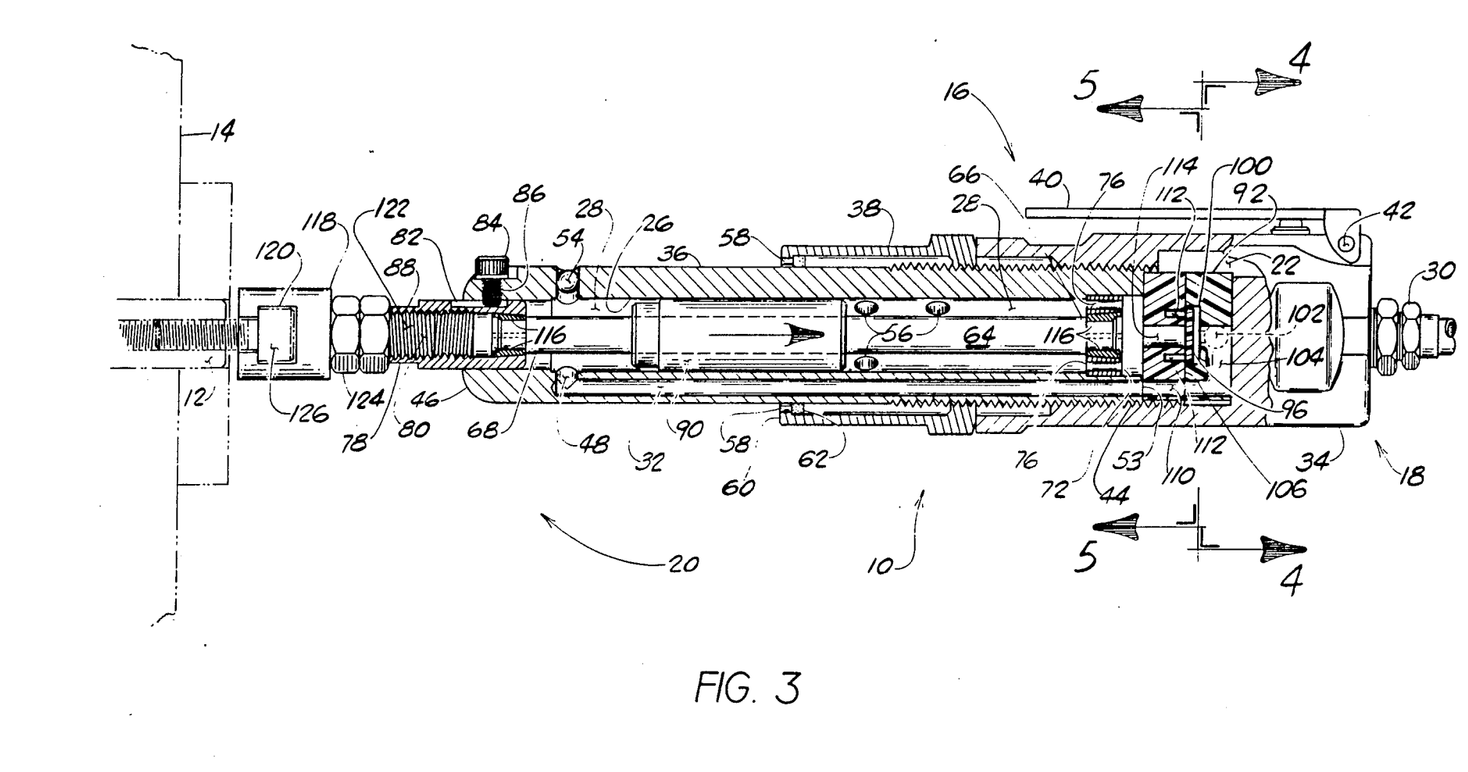
FIG. 3 is a longitudinal cross-sectioned view of the device shown in FIG. 2, illustrating the intake stroke of the device.

Illustrated in FIG. 1, 2, and 3 is a pneumatic device 10 for removing a workpiece 12, such as a pin, dowel, rod, nail, and the like, embedded in a material 14, such as wood, metal, steel, concrete, molded plastic and ceramic, etc., as well as human and animal bone, and also for removing and extracting pulleys, bearings, inner races, and shafts. More specifically, the present invention is a pneumatically actuated device that employs a reverse impact hammer striking effect to remove and extract the above-mentioned workpieces embedded in a variety of materials, including, but not limited to, the above-described materials.

As illustrated in FIG. 1, 2, and 3, the preferred embodiment of the present invention includes an elongated, generally cylindrical main housing 16. The main housing 16 has a handle gripping end 18 for manual gripping by a workman and an opposite tool-holding end 20 which is adjacent the workpiece 12 being removed from the material 14. At the gripping end 18 of the main housing 16 is an interior air distribution chamber 22, which is in air flow communication with an air inlet passage 24. The main housing 16 also includes an elongated, cylindrical inner bore 26 which defines a central chamber 28 extending substantially the length of the main housing 16. An external air supply means (not shown) supplies pressurized air into the inlet passage 24 whereupon the pressurized air is directed into the distribution chamber 22 and then, as shall be more fully described hereinafter, into the central chamber 28. The air supply means may include a conventional air compressor that would include a compressed air tank, a filter, a regulator, an oiler, and then tubing which would be connected at one end to the inlet passage 24 by an air inlet fitting 30. The use of a filter, an air line pressure regulator, and a lubricator mounted adjacent to the device 10 is recommended, and in the present invention, 90 psi of clean dry air is required at the device 10 for satisfactory performance during operation with an average air consumption of 5 cfm. The device 10 operates at a maximum of 90 psig; higher pressures may cause injury as well as cause damage to structural components by placing them under loads and stresses for which they were not designed.

Eccentric to the central chamber 28 and located within the main housing 16 is a lateral side passage 32 generally parallel with and extending substantially the same length as the central chamber 28. As will be more fully described hereinafter, pressurized air from the distribution chamber 22 is directed into the lateral passage 32 as well as the central chamber 28 during operation of the device 10.

The main housing 16 has three primary structural components: a tool handle 34, a barrel 36, and a muffler housing 38. The handle 34 is a generally elongated structure which, in cross-section, is octagonal. As shown in FIG. 1, the inlet passage 24 and the distribution chamber 22 are located within the handle 34. A hand-operated throttle lever 40 is pivotally mounted to the handle 34 by a lever pin 42 and is depressed during operation of the device 10 to allow pressurized air from the air compressor to enter through the inlet passage 24 where it is directed to the distribution chamber 22 and then into the central chamber 28 and the lateral passage 32. The inlet passage 24 is threaded so that the fitting 30, such as a ¼-inch fitting, can be threadably secured thereto so that a hose or tube from the compressor can be attached to the externally-projecting fitting 30. The inlet valve assembly 43 fits within the handle 34 and operates in conjunction with the lever 40.

The handle 34 is an essentially hollow structure having a bore extending substantially therethrough, concentric to and in air flow communication with the distribution chamber 22. Inserted into the handle 34 is the barrel 36. The barrel 36 is an elongated cylindrical structure externally threaded at an inner barrel end 44 and having an opposite, rounded, non-threaded, outer barrel end 46. The inner bore 26 is located within the barrel 36 and extends from the inner end 44 to the rounded end 46. The barrel 36 is adapted for removable securement into the handle 34; the inner end 44 is externally threaded for insertion into the tool handle bore as shown in FIG. 2 and 3. In addition, the barrel 36 also includes the lateral passage 32 and an air pressure passageway 48 located adjacent the outer end 46 which connects the lateral passage 32 to the central chamber 28 so that pressurized air can flow between the lateral passage 32 and the central chamber 28 during operation of the device 10. The barrel 36 also includes a pair of blind, barrel retaining pin holes 50 located on an annular flat face 52 of the barrel 36 at the inner end 44 and spaced 180° from each other. The opening 53 for the lateral passage 32 is adjacent one of the pin holes 50.

A plug 54, as shown in FIG. 2 and 3, is inserted into that portion of the drilled through-hole at the outer end 46 of the barrel 36 for creating the air pressure passageway 48. The barrel 36 also includes a plurality of spaced-apart barrel exhaust ports 56 which permit air to be exhausted to the atmosphere and whose function will be more fully described hereinafter. The pin holes 50 are utilized to maintain proper alignment of the barrel 36 when it is disposed within the handle 34.

The muffler housing 38 is generally cylindrical and elongated in shape, and is adapted for threadable securement onto and encompassing the barrel 36 adjacent the inner end 44, and abuts the handle 34 when disposed in its operative position. However, the portion of the muffler housing 38 that abuts the handle 34 is hexagonal in shape. In order to allow air to be exhausted to the atmosphere, the muffler housing 38 has a plurality of muffler exhaust holes 58 equally spaced and located on an annular flange 60 at the end of the elongated, cylindrical portion of the muffler housing 38 opposite the portion of the muffler housing 38 that abuts the handle 34. Before the muffler housing 38 is inserted on the barrel 36, a cylindrical muffler 62 is dropped into the bore of the muffler housing 38 and is positioned inside the flange 60 and adjacent the plurality of exhaust holes 58. As illustrated in FIG. 2 and 3, there is an annular space or clearance area between the barrel 36 and the muffler housing 38 which extends the length of the cylindrical portion of the muffler housing 38 and permits the exhaustion of air through the muffler exhaust holes 58 out to the atmosphere. The handle 34 and the muffler housing 38 are concentrically aligned when disposed in their operative position.

Figure 7:
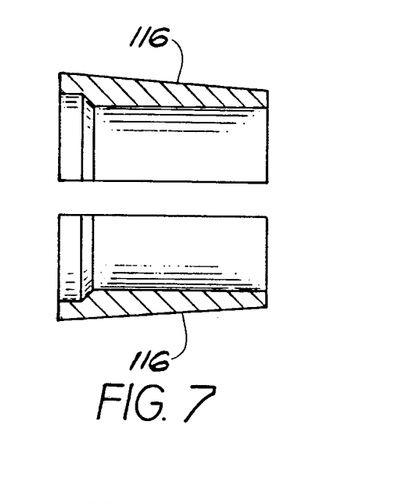
FIG. 7 is a fragmentary side elevational view of structural components of the device first shown in FIG. 1.
Figure 8:
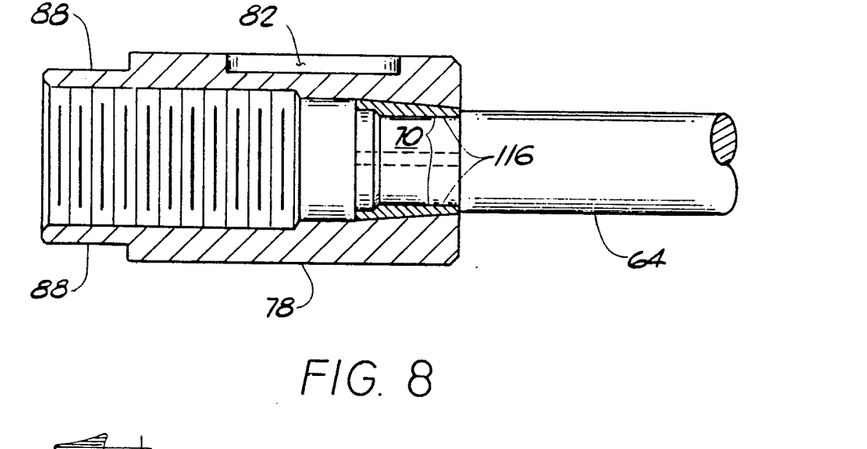
FIG. 8 is an enlarged fragmentary view of the device first illustrated in FIG. 1.

As illustrated in FIG. 1, 2, and 3, an elongated, cylindrical shaft 64 is disposed within the central chamber 28 and is adapted for linear reciprocable movement therein to effect the extraction and removal of the workpiece 12 from the material 14. The shaft 64 extends substantially the length of the inner bore 26 and is concentric with the central chamber 28; in addition, the shaft 64 has an inner end 66 which is disposed adjacent to the inner end 44 and an opposite outer end 68 which is disposed adjacent the outer end 46. As shown in FIG. 1, 7, and 8, a shallow annular recess or trough 70 is located at both the outer end 68 and the inner end 66, and the diameter of this trough 70 is slightly smaller than the diameter of the shaft 64 itself. Pressurized air flows in the annular space of the central chamber 28 between the shaft 64 and the inner bore 26 of the barrel 36.

A disc-shaped anvil 72 is adapted for removable securement or mounting to the shaft 64 at the inner end 66 thereof and adjacent the distribution chamber 22. More specifically, the anvil 72 is mounted to the shaft 64 by inserting the shaft 64 into a conical-shaped, tapered anvil bore 74 of the anvil 72. The inside diameter of the anvil bore 74 has a taper or angle of 4°, the purpose of which will be described more fully hereinafter. Furthermore, as illustrated in FIG. 1, 2, and 3, the anvil 72 includes a plurality of lateral, spaced-apart anvil air holes 76 for permitting pressurized air flow therethrough. The anvil 72 includes six air holes 76 equally spaced about the periphery of the anvil 72, and drilled therethrough. When the anvil 72 is mounted to the inner end 66 of the shaft 64, the anvil bore 74 is concentric with the shaft 64 and the central chamber 28. Also, when the anvil 72 is disposed in its operative position, the anvil 72 is circumjacent to the trough 70 located at the inner end 66 thereof.

FIG. 1, 2, 3, and 8 illustrate a tool holder 78 which is adapted for removable mounting or securement to the outer end 68 of the shaft 64 adjacent the holding end 20 of the main housing 16. More specifically, the holder 78 is a generally cylindrical, elongated structure which partially protrudes from the barrel 36 when the holder 78 is disposed in its operative position. As illustrated in FIG. 2 and 3, the holder 78 partially protrudes from the outer end 46 and is partially mounted therein with the outer surface of the holder 78 contiguously abutting the inner bore 26 of the barrel 36. The holder 78 includes a tool holder bore 80 that extends therethrough and which is partially threaded and partially tapered. The partially threaded portion of the bore 80 projects out of the barrel 36, and the portion of the bore 80 which is conical-shaped and tapered is disposed within the barrel 36 when the holder 78 is disposed in its operative position. The bore 80 is concentric with the anvil bore 74, the shaft 64, and the inner bore 26 when the device 10 is disposed in its operative position, and the portion of the bore 80 which is conical-shaped has an inside diameter tapered at an angle of 4°. Moreover, when the holder 78 is mounted to the shaft 64, the portion of the bore 80 which is conical-shaped and tapered at an angle of 4° is circumjacent the trough 70 located at the outer end 68 of the shaft 64.

The holder 78 also includes an elliptical slot 82 formed on the outer surface thereof; the slot 82 is not drilled through, but is recessed into, the holder 78 for receiving a retaining screw 84, as illustrated in FIG. 1, 2, and 3. The screw 84 is inserted through a lateral bore 86 at the holding end 20 of the main housing 16 or, more specifically, the lateral bore 86 is drilled through the barrel 36 at the outer end 46 to the inner bore 26 so that it registers with the central chamber 28 when the holder 78 is not inserted into the barrel 36. When the holder 78 is mounted to the shaft 64 so that it partially protrudes from and is partially set within the barrel 36, the slot 82 is encompassed by the inner bore 26; however, as shown in FIG. 2 and 3, a portion of the slot 82 can protrude out of the outer end 46. The slot 82 receives the screw 84 and thus prevents rotation of the holder 78 and the shaft 64 during operation of the device 10.

As will be more fully described hereinafter, because the holder 78 is mounted to the shaft 64 without the use of pins, threading, or welding, side loading and excessive stress on the shaft 64 is substantially reduced and, because a portion of the holder 78 itself is mounted within and is contiguously encompassed by the inner bore 26, side loading that does occur is absorbed by the holder 78 because the holder 78 reacts against the inner bore 26, thus the life expectancy of the shaft 64 is increased and the tendency of the shaft 64 to fracture is decreased. A pair of oppositely-disposed wrench flats 88 are located on that part of the outer surface of the holder 78 which projects out of the barrel 36. When the device 10 is being assembled, the wrench flats 88 can be used for firmly gripping the holder 78 and wedging it onto the outer end 68 of the shaft 64, as shall be more fully described hereinafter.

There is shown in FIG. 1, 2, and 3 a piston 90 slidably disposed on the shaft 64 and adapted for reciprocal linear movement thereon, the linear movement of the piston 90 actuated by the continuous variations of air pressure that occur within the central chamber 28 and the lateral passage 32 during the operation of the device 10. The piston 90 is adapted to strike the anvil 72 on a power stroke, pulling and moving the shaft 64 in a reverse direction toward the handle end 18, thus causing extraction of the workpiece 12. When the piston 90 strikes the anvil 72 on the power stroke, or reverse impact stroke, the shaft 64 itself is pulled away from the workpiece 12 embedded in the material 14 and toward the handle end 18 of the main housing 16, i.e., toward the handle 34. Hence, the name "pneumatically driven reverse impact device". Because the piston 90 cycles on the shaft 64 at a very high rate of speed (an optimum of 33 cycles per second) the continuous reverse impact striking of the piston 90 against the anvil 72 effects the quick and efficient removal of the workpiece 12 embedded in the material 14. When the device 10 is operating at 90 psi, the piston 90 is capable of delivering 2,000 blows per minute to the anvil 72. At a maximum force of 1,500 pounds, the amount of force exerted on the anvil 72 by the piston 90 is 3,739 pounds per square inch.

When the device 10 is in operation, the fitting 30 is threaded into the inlet passage 24 of the handle 34. Pressurized air is delivered from the compressor and through the fitting 30 into the inlet passage 24, and from there, pressurized air is directed into the distribution chamber 22 of the handle 34. Located within the distribution chamber 22 is a valve regulation means, which is conventional in the art, for regulating and directing the flow of pressurized air into the central chamber 28 and the lateral passage 32. The valve regulation means, as shown in FIG. 1-5, includes an upper valve block 92 and a flipper valve 96. During operation of the device 10, the flipper valve 96 is adapted to "float" between the upper block 92 and a structural component to be described hereinafter.

Figure 4:
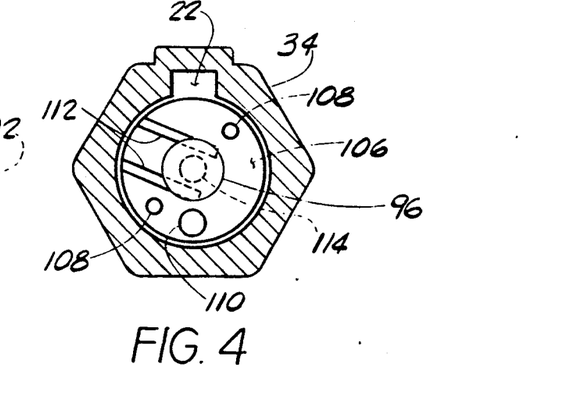
FIG. 4 is a sectional view taken along lines 4—4 of FIG. 3.
Figure 5:
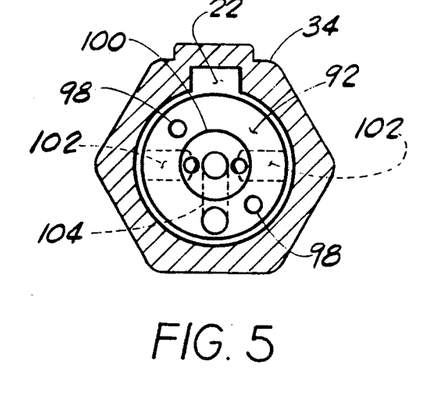
FIG. 5 is a sectional view taken along lines 5—5 of FIG. 3.
Figure 6:
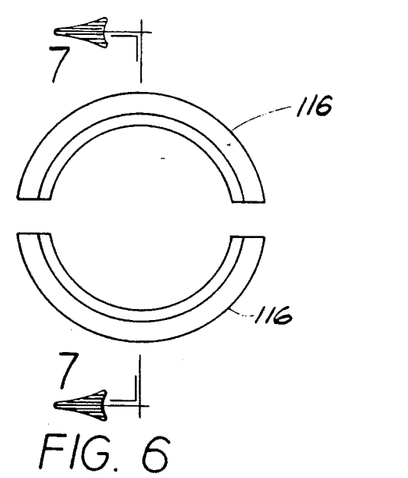
FIG. 6 is a front elevational view of structural components of the device first illustrated in FIG. 1.

As shown in FIG. 1 and 4, the upper block 92 is disc-shaped, cylindrical, and adapted to fit snugly within the distribution chamber 22. The upper block 92 includes a pair of blind retaining pin holes 98 that are spaced 180° from each other and are adjacent the periphery of the block 92, a centrally located circular recess 100 within which the flipper valve 96 can float and set against, and a pair of lateral air passages 102 spaced 180° from each other and which extend from opposite peripheral edges of the block 92 into the recess 100. The passages 102 are in air flow communication with the recess 100 and receive air from the distribution chamber 22. As shown in FIG. 2 and 3, the upper block 92 also includes a U-shaped, rear passageway 104 in air flow communication with the lateral passage 32. The rear passageway 104 is also in air flow communication with the recess 100 and is located 90° from each lateral passage 102. It should be noted that the passages 102 are in direct air flow communication with the recess 100 and are in indirect air flow communication with the rear passageway 104. Concomitant with pressure variations occurring within the central chamber 28 from the reciprocable cycling of the piston 90 and the exhaustion of air out of the ports 56, pressurized air from the distribution chamber 22 is continuously entering the passages 102 of the upper block 92 whereupon the pressurized air is directed into the recess 100 and, from there, to the rear passageway 104.

Pressure variations occurring within the central chamber 28 also cause the flipper valve 96 to float within the recess 100 closing off the recess 100, thus blocking air flow entering the lateral passages 102 from reaching the recess 100. The flipper valve 96 acts as a diaphragm as it floats within the recess 100. Also disposed within the distribution chamber 22 is a cylindrical lower valve block 106 which is concentrically aligned and contiguous with the upper block 92. As shown in FIG. 2 and 3, a peripheral portion of the lower block 106 opposite the upper block 92 also abuts the annular face 52 of the barrel 36. The lower block 106 includes a pair of lower valve retaining through-holes 108 which are spaced 180° apart and are aligned with the blind holes 98 of the upper block 92. In addition, the lower block 106 includes a lateral side aperture 110 adjacent the periphery of the lower block 106 for allowing pressurized air flow therethrough. When the lower block 106 is disposed in its operative position, the aperture 110 is aligned and in air flow communication with the lateral passage 32 of the barrel 36 and a portion of the rear passageway 104 of the upper block 92. The lower block 106 also includes a pair of spaced-apart, parallel inlet passageways 112 that extend from the peripheral edge of the lower block 106 to the center thereof. The inlet passageways 112 continuously receive pressurized air from the distribution chamber 22 and direct pressurized air into the recess 100.

Concomitant with pressure variations occurring in the central chamber 28 due to the cyclical and reciprocable movement of the piston 90 and the exhaustion of air through the ports 56, pressurized air entering the inlet passageways 112 will push the flipper valve 96 into the recess 100 to block air from entering the recess 100 from both lateral passages 102 and to allow the pressurized air to flow into a central lower valve block aperture 114 which extends through the center of the lower block 106 and is in air flow communication with the central chamber 28 as shown in FIG. 2. It should be noted that the inlet passageways 112 are not in direct air flow communication with the central aperture 114. The central aperture 114 is axially aligned with but has a smaller diameter than the recess 100. When the flipper valve 96 has been pushed against the lower block 106 due to the pressure variations that are occurring continuously within the central chamber 28 during the operation of the device, as shown in FIG. 3, pressurized air flow from the parallel passageways 112 is blocked from reaching the central aperture 114. It should be noted that when the piston 90 strikes the anvil 72 on the reverse impact or power stroke, the anvil 72 will not be pushed so as to impinge upon the lower block 106. Only when the device 10 is running without attachment to a workpiece 12 will the force of the piston 90 striking the anvil 72 cause the anvil 72 to impinge upon the lower block 106. Therefore, the device 10 should not be operated without a load, i.e., without attachment to the workpiece 12 embedded in the material 14.

Illustrated in FIG. 1, 2, 3, 6, 7, and 8 are a plurality of retaining clips 116 which are mounted respectively at the inner end 66 and outer end 68 of the shaft 64. More specifically, for the device 10 of the present invention, a total of four retaining clips 116 are utilized, with two clips 116 mounted in the trough 70 at the outer end 68 of the shaft 64 and two clips 116 mounted in the trough 70 at the inner end 66 of the shaft 64. Each clip 116 is a half-circle-shaped structure having an outer surface diameter tapered at an angle of 4°. Each pair of clips 116 is dropped onto the respective trough 70 on the shaft 64. Thus, when each pair of clips 116 are disposed in their operative position, they form a circular, tapered, and continuous outer surface circumjacent the shaft ends 66 and 68 and which contiguously encompass each trough 70 located at each respective shaft end 66 and 68. The tapered outer surface of the clips 116 matches the bore 74 of the anvil 72 and the bore 80 of the holder 78. Thus, when each pair of clips 116 are disposed on the respective shaft ends 66 and 68, their continuous tapered surface diameters mate and match with the inside diameter of the bore 74 of the anvil 72 and the bore 80 of the holder 78.

In assembling the anvil 72 and the holder 78 to the shaft 64, a pair of clips 116 are mounted or dropped onto the trough 70 at the inner end 66 and the outer end 68 of the shaft 64. The anvil 72 and the holder 78 can then be mounted to the shaft 64 by wedging the bore 74 of the anvil 72 against the tapered surface of the pair of clips 116 that encompass the trough 70 at the inner end 66, and by pressing the holder 78 onto the pair of clips 116 that encompass the trough 70 at the outer end 68 so that the bore 80 mates with and is wedged against the tapered surface of the clips 116. The assembly of the shaft 64 is thus simplified because each pair of clips 116 are dropped onto the trough 70 and then the anvil 72 and the holder 78 are pressed and wedged onto each respective pair of clips 116. By firmly pressing the holder 78 and the anvil 72 onto each respective pair of clips 116, and because of the mechanical forces acting on the assembly now comprising the shaft 64 with the holder 78 and the anvil 72 mounted thereon, the holder 78 and the anvil 72 are securely held onto the shaft 64. Thus, the need to thread, pin, or weld the outer end 68 and the inner end 66 of the shaft 64 to retain the anvil 72 and the holder 78 is obviated by the use of the clips 116 and the shaft 64 is much stronger than a similar shaft of the same diameter. Pinning, threading, or welding the ends 66 and 68 of the shaft 64 to retain the holder 78 and the anvil 72 substantially weakens the shaft 64 and increases the stress and the side load thereon. Utilizing the clips 116 of the present invention alleviates undue stress and side load on the shaft 64, and shaft stress is also relieved by the annular distribution of mechanical vibrations transmitted and received therein during removal of the workpiece. After assembling the holder 78 and the anvil 72 to the respective ends 66 and 68 of the shaft 64, the holder 78, shaft 64, and anvil 72 can be considered a one-piece unit securely fastened together for unitary linear reciprocal movement within the central chamber 28. The piston 90 is thus trapped on the shaft 64 for linear and cyclical movement between the holder 78 and the anvil 72 within the inner bore 26.

The device of the present invention includes several pieces which can be removably secured and attached to the holder 78 so that various types of workpieces as well as inner races, bearings, pulleys, and shafts can be removed from the aforementioned material or from other structural components to which they are connected or assembled. The device 10 of the present invention includes a screw adapter means which is removably secured to the holder 78 and also to the workpiece 12 for facilitating the removal of the workpiece 12 from the material 14. More specifically, the screw adapter means includes, as shown in FIG. 2 and 3, a cap screw adapter 118 having a milled pocket 120 and a threaded shaft 122 which is threadably inserted into the portion of the bore 80 which is threaded. Cap screw adapters come in various sizes with common sizes being $\frac{1}{4}''$, 5/16'', and $\frac{3}{8}''$. If a dowel, pin, or rod projecting out of the material 14 has a tapped hole, a standard cap screw can be threaded into the tapped hole. The appropriately sized cap screw adapter is then securably threaded into the holder 78 (the holder 78 already being mounted to the barrel 36). Referring to FIG. 2 and 3, one or several jam nuts 124 can be threaded onto the shaft 122 for further securing the adapter 118 to the holder 78. The adapter 118 has a milled pocket 120 which can fit snugly over the head of the cap screw 126. When the device 10 is in operation, the pulling effect caused by the reverse impact striking of the piston 90 against the anvil 72 will thus exert a pulling effect on the holder 78 as aforedescribed, and the holder 78 will pull the adapter 118 attached to the head of the cap screw 126. This will cause the dowel, pin, or rod, within which the shaft of the cap screw 126 is threaded, to be removed and extracted from the material 14.

Figure 9:
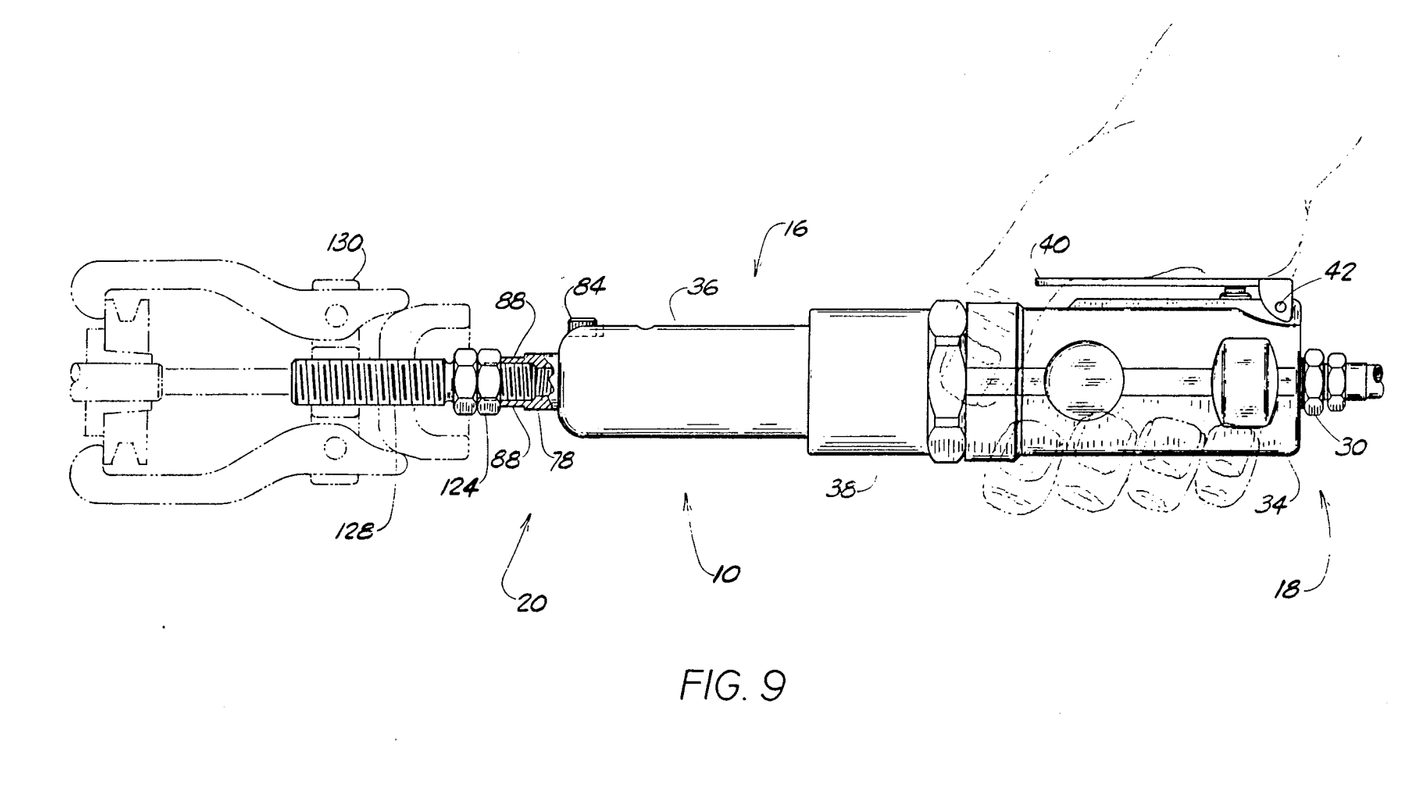
FIG. 9 is a cross-sectioned longitudinal view of the device, illustrating the use of the device in conjunction with a stud adapter and peripheral tooling from existing slide hammer sets.

The device 10 of the present invention also includes a stud adapter means which can be adapted to extract and remove pulleys, inner races, bearings, and shafts. The stud adapter means, shown in FIG. 9, enables the device 10 of the present invention to be used with existing manual slide-hammer peripheral attachments and peripheral tooling from slide-hammer sets, such as jaws which are used to pull and extract inner races or bearings from other structural components. The stud adapter means of the present invention includes a stud adapter 128 adapted for removable securement to the holder 78. The stud adapter 128 has a first threaded end for threadable insertion and attachment into the partially threaded portion of the bore 80 and a second threaded end for threadable attachment to peripheral tooling from existing slide hammer sets, such as a jaw puller 130 utilized for the aforedescribed purpose. The first threaded end of the stud adapter 128 is a $\frac{1}{2}$-20 thread and the second threaded end which attaches to the peripheral tooling is a $\frac{5}{8}$-18 thread. Thus, most standard jaw pullers can be attached to the second threaded end of the stud adapter 128 of the present invention.

FIG. 1, 2, and 3 illustrate a pair of elongated, cylindrical retaining pins 132 which are employed to keep the upper block 92, the lower block 106, and the barrel 36 axially aligned when all three structural components are disposed within the handle 34. The pins 132 fit and protrude through the through-holes 108 of the lower block 106, and are inserted into the blind holes 98 of the upper block 92. The upper block 92 and the lower block 106 are thus aligned when each pin 132 is inserted as described. Each pin hole 50 located on the annular face 52 of the inner end 44 of the barrel 36 then receives one of the pins 132. This maintains the alignment of the upper block 92 with the lower block 106, and further maintains the alignment of both blocks 92 and 106 with the barrel 36 so that the lateral passage 32 is aligned and in air flow communication with the aperture 110 of the lower block 106 and the rear passageway 104 of the upper block 92.

In operation, the throttle lever 40 is depressed, permitting pressurized air from the air compressor to pass through the inlet passage 24 and then enter the distribution chamber 22. The piston 90 and the flipper valve 96 may be in an intermediate position just before depression of the throttle lever 40 due to the angle at which the device 10 is pointed for removing the workpiece 12 from the material 14. For instance, the flipper valve 96 may start from an initial position of being against the recess 100, thus blocking off the egress of air from the lateral passages 102, the pressurized air would thus enter the two passageways 112 of the lower block 106. The pressurized air would then pass through the central aperture 114 and into the gap of approximately ⅛-inch between the anvil 72 and the lower block 106. The pressurized air would then flow through the anvil holes 76 and into the central chamber 28, forcing the piston 90 to slidably move on the shaft 64 toward the holder 78. While this is occurring, the pressurized air maintains the flipper valve 96 in the recess 100 and against the upper block 92.

As the piston 90 moves forward in the central chamber 28, the piston 90 is forcing air through the passageway 48 and into the lateral passage 32, and thence into the rear passageway 104 leading to the rear of the upper block 92. Concomitant with pressurized air entering the lateral passage 32 and being directed toward the rear of the upper block 92, the pressurized air behind the forwardly moving piston 90 is being exhausted through the ports 56 (of which the present invention includes six), and thence through the muffler holes 58 to the atmosphere.

Thus, when the piston 90 clears the ports 56 in its forward travel, the area of the inner bore 26 behind the piston 90 is depressurized. Before the piston 90 reaches the area of the inner bore 26 adjacent the holder 78, the pressure has increased in the lateral passage 32 to the point where the pressurized air entering the recess 100 via the rear passageway 104 and the passages 102 of the block 92 pushes the flipper valve 96 against the lower block 106. The air supply to the piston 90 is thus cut off by the flipper valve 96 abutting the lower block 106 and blocking the air from exiting the passageways 112 and entering the area of the central chamber 28 rearward of the piston 90. FIG. 3 illustrates this state. The piston 90 is prevented from striking the holder 78 by the residual air pressure existing between the piston 90 and the area of the central chamber 28 forward thereof. In addition, the barrel 36 is stepped in the area of the inner bore 26 adjacent the end 46, thus preventing the piston 90 from reaching and striking the holder 78 on the forward motion of the piston 90.

With the flipper valve 96 pushed up against the lower block 106, the egress of pressurized air from the passageways 112 is now blocked. Pressurized air from the distribution chamber 22 is then directed through the passages 102, into the rear passageway 104 and thence into the lateral passage 32 and into the central chamber 28 in the area between the holder 78 and the piston 90. Thus, the pressurized air forces the piston 90 to reverse its direction and move toward the anvil 72, as shown in FIG. 3, on the reverse or impact stroke. The piston 90 strikes the anvil 72 causing the shaft 64, the anvil 72, and the holder 78 (the unitary shaft assembly) to be pulled toward the handle 34, thus causing the workpiece 12 to be pulled from the material 14. When the piston 90 strikes the anvil 72, the ports 56 are uncovered, permitting air to be exhausted to atmosphere and causing a depressurization of the central chamber 28 in the area between the piston 90 and the holder 78.

The net effect of this reverse impact stroke is exactly opposite of a hammer., rather, instead of sharp blows to an object or the workpiece 12, a series of sharp jerking or pulling motions is effected by the piston 90 rapidly and continuously striking the anvil 72 during operation of the device 10. As the piston 90 gets closer to the anvil 72 on the return impact stroke, pressurized air is being pushed by the piston 90 through the anvil holes 76 and then through the aperture 114, thus pushing the flipper valve 96 away from the aperture 114, causing a reversal of the air flow which starts the piston 90, after it has struck the anvil 72, on its set-up stroke back toward the holder 78.

It will be understood that various changes and modifications may be made in the details of the illustrative embodiments within the scope of the appended claims, but without departing from the spirit of this invention.

We claim:

1. A pneumatic device actuated by a pressurized air supply means for removing a workpiece, such as a pin, dowel, rod, and the like, embedded in a material, and for extracting pulleys, bearings, shafts, inner races, and the like, comprising:
    an elongated, generally cylindrical main housing having an air distribution chamber at a handle gripping end and an opposite tool holding end;
    an inner bore extending substantially the length of the main housing and defining an elongated central chamber;
    a lateral side passage parallel with and extending substantially the same length as the chamber;
    valve regulation means for regulating and directing the flow of pressurized air into the central chamber, the valve regulation means positioned within the air distribution chamber;
    a shaft slidably disposed within the central chamber for linear reciprocable movement therein to effect removal of the workpiece;
    a tool holder mounted to the shaft and protruding partially from the main housing, the tool holder for attachment to the workpiece and for mounting to the shaft within the main housing for relieving excessive stress and side load on the shaft;
    the tool holder further characterized by having a conical-shaped, tapered tool holder bore within which the shaft is mounted;
    a cylindrical anvil mounted to the shaft opposite the tool holder having a plurality of lateral, spaced-apart air holes for permitting pressurized air flow therethrough, the anvil further characterized by having a conical-shaped, tapered anvil bore within which the shaft is mounted;
    a piston slidably disposed on the shaft for reciprocable linear movement thereon, the piston adapted to strike the anvil on a power stroke thus moving the shaft in a reverse direction toward the handle gripping end causing extraction of the workpiece;
    two pairs of tapered, half-circle-shaped retaining clips with one pair of clips mounted to each opposite end of the shaft, each pair of clips forming a tapered outer surface which matches and is wedged against, respectively, the tool holder bore and the anvil bore thus securing the tool holder and the anvil to the shaft; and
    a stud adapter means to attach peripheral tooling from slide hammer sets to the tool holder for effecting the extraction of pulleys, bearings, and shafts.

2. The device of claim 1 further comprising a screw adapter means for receiving cap screws of various sizes which are fastened to the workpiece, the screw adapter means removably secured to the tool holder and the cap screw for facilitating the removal of the workpiece from the material.

3. The device of claim 2 wherein the screw adapter means includes a cap screw adapter having a milled pocket and a threaded shaft, the milled pocket for receiving the cap screw fastened to the workpiece and the threaded shaft for securement to the tool holder.

4. The device of claim 1 further comprising a stud adapter adapted for removable securement to the tool holder, the stud adapter having a first threaded end for attachment to the tool holder and a second threaded end for attachment to jaw pullers from slide hammer sets.

5. The device of claim 1 wherein the tool holder includes an elliptical slot formed on the tool holder, the slot located substantially within the main housing when the tool holder is mounted to the shaft and adapted to prevent rotation of the shaft during linear reciprocable movement within the central chamber.

6. The device of claim 5 further comprising a retaining screw inserted through the main housing and into the slot, for preventing tool holder rotation when the device is in operation.

7. The device of claim 6 wherein the side loading on the shaft is absorbed by the tool holder reacting against the inner bore of the main housing.

8. The device of claim 1 wherein the conical-shaped tapered bore of the anvil has an angle of 4°.

9. The device of claim 1 wherein the conical-shaped tapered tool holder bore has an angle of 4°.

10. The device of claim 1 wherein each pair of clips, when disposed in their operative position, relieve shaft stress by receiving the annular distribution of mechanical vibrations that occur during workpiece removal.

* * * * *